United States Patent [19]

Skuballa et al.

[11] Patent Number: 4,827,017

[45] Date of Patent: May 2, 1989

[54] NOVEL CARBACYCLINS, PROCESSES FOR THEIR PRODUCTION AND THEIR USE AS MEDICINAL AGENTS

[75] Inventors: Werner Skuballa; Bernd Raduechel; Helmut Vorbrueggen; Ekkehard Schillinger; Claus-Steffen Stuerzebecher, all of Berlin, Fed. Rep. of Germany

[73] Assignee: Schering Aktiengesellschaft, Berlin and Bergkamen, Fed. Rep. of Germany

[21] Appl. No.: 21,102

[22] Filed: Mar. 3, 1987

Related U.S. Application Data

[63] Continuation of Ser. No. 866,667, May 27, 1986, which is a continuation of Ser. No. 709,731, Mar. 8, 1985, abandoned.

[30] Foreign Application Priority Data

Mar. 8, 1984 [DE] Fed. Rep. of Germany ....... 3408699

[51] Int. Cl.$^4$ ............................................ C07C 177/00
[52] U.S. Cl. ....................................... 560/56; 562/466
[58] Field of Search ........................... 560/56; 562/466; 514/130

[56] References Cited

U.S. PATENT DOCUMENTS 4,692,464 9/1987 Skuballa et al. ..................... 560/56

FOREIGN PATENT DOCUMENTS 2070596 9/1981 United Kingdom .

Primary Examiner—Paul J. Killos
Attorney, Agent, or Firm—Millen & White

[57] ABSTRACT

Carbacyclin derivatives of Formula I

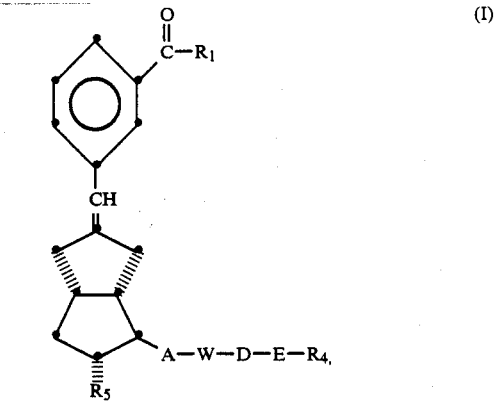

wherein
$R_1$ is $OR_2$ wherein $R_2$ is hydrogen, $C_1$-$C_{10}$-alkyl, $C_3$-$C_{10}$-cycloalkyl, $C_6$-$C_{10}$-aryl,

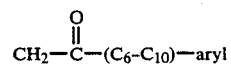

or a heterocyclic residue, or
$R_1$ is $R_3$ wherein $R_3$ is $C_1$-$C_{10}$-alkyl, $C_3$-$C_{10}$-cycloalkyl, $C_6$-$C_{10}$-aryl, $C_7$-$C_{14}$-aralkyl or a heterocyclic residue,
A is —$CH_2$—$CH_2$—, trans—CH=CH— or —C≡C—,
W is a free or functionally modified hydroxymethylene group or a free or functionally modified $$-\underset{OH}{\underset{|}{\overset{CH_3}{\overset{|}{C}}}}-\text{group}$$

wherein the OH-group can be in the $\alpha$- or $\beta$-position,
D is

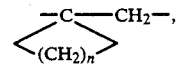

a straight-chain, saturated alkylene group of 1-10 carbon atoms, or a branched, saturated or a straight-chain or branched, unsaturated alkylene group of 2-10 carbon atoms, each of which can optionally by substituted by fluorine atoms,
n is the number 1, 2 or 3,
E is —C≡C— or —$CR_6$=$CR_7$— wherein $R_6$ and $R_7$ differ from each other and one is hydrogen and the other alkyl of 1-5 carbon atoms, or one is hydrogen and the other is halogen, or
E can also be —$CH_2CH_2$— when $R_1$ is $R_3$,
$R_4$ is $C_{1-10}$-alkyl, $C_3$-$C_{10}$-cycloalkyl, optionally substituted $C_6$-$C_{10}$-aryl or a heterocyclic group,
$R_5$ is a free or functionally modified hydroxy group and, when $R_2$ is hydrogen, the salts thereof with physiologically compatible basis; are useful as medicinal agents.

14 Claims, No Drawings

NOVEL CARBACYCLINS, PROCESSES FOR THEIR PRODUCTION AND THEIR USE AS MEDICINAL AGENTS

This is a continuation, of application Ser. No. 866,667, filed May 27, 1986, which is a continuation of Ser. No. 709,731, filed Mar. 8, 1985, now abandoned.

BACKGROUND OF THE INVENTION

This invention relates to novel carbacyclin derivatives, processes for their production as well as their use as medicinal agents.

The precursor of carbacyclins, prostacyclin, was isolated in 1976 and clarified with respect to its structure in the same year (Prostaglandins 12: 915, 1976). For some time, the designation $PGI_2$ has become accepted for prostacyclin, as a prostaglandin abbreviation. Correspondingly, carbacyclins are also called 6a-carbaprostaglandins $I_2$.

The nomenclature of the compounds of this invention is based on a proposal by Morton and Brokaw (J. Org. Chem. 44: 2280[1979]. The synthesis of these compounds yields in all cases two double-bond isomers characterized by the symbols (5E) or (5Z). By substituting the top chain, for example, by an aromatic residue, structural formulae are obtained which can be described as follows:

(5E)—2,3,4-Trinor-1,5-inter-m-phenylene-6a-carbaprostaglandin $I_2$ (5Z)—2,3,4-Trinor-1,5-inter-m-phenylene-6a-carbaprostaglandin $I_2$ Such prostacyclin analogs have been disclosed in DOS No. 3,146,278 and European Patent No. 0062 902.

Based on their biological and pharmacological properties, prostacyclins and their analogs are suitable for therapy and prophylaxis of thromboses, infarctions and other cardiovascular diseases. The duration of activity of these compounds is frequently still too brief for therapeutic purposes. For this reason, all structural modifications of known $PGI_2$ derivatives aim at prolonging the period of efficacy, increasing the selectivity of activity, and simultaneously reducing the effective dose.

SUMMARY OF THE INVENTION

Accordingly, it is an object of this invention to provide new such prostaglandin compounds having such valuable pharmacological properties.

Upon further study of the specification and appended claims, further objects and advantages of this invention will become apparent to those skilled in the art.

It has now been found that, by introduction of a triple bond in the 18,19- or 19,20-position of the lower chain of the 2,3,4-trinor-1,5-inter-m-phenylene-6a-carbaprostaglandin $I_2$ analogs, efficacy can be improved, selectivity can be increased and duration of activity can be lengthened.

These objects have been achieved by providing carbacyclin derivatives of Formula I wherein
$R_1$ is $OR_2$ wherein $R_2$ is hydrogen, $C_1$–$C_{10}$-alkyl, $C_3$–$C_{10}$-cycloalkyl, $C_6$–$C_{10}$-aryl, $$CH_2-\overset{O}{\underset{\|}{C}}-(C_6-C_{10})-aryl$$

or a heterocyclic residue, or $R_1$ is $R_3$ wherein $R_3$ is $C_1$–$C_{10}$-alkyl, $C_3$–$C_{10}$-cycloalkyl, $C_6$–$C_{10}$-aryl, $C_7$–$C_{14}$-aralkyl or a heterocyclic residue, A is —$CH_2$—$CH_2$—, trans-CH=CH— or —C≡C—, W is a free or functionally modified hydroxymethylene group or a free or functionally modified $$-\underset{\underset{OH}{|}}{\overset{\overset{CH_3}{|}}{C}}-group$$

wherein the OH-group can be in the α- or β-position,

D is a straight-chain, saturated alkylene group of 1-10 carbon atoms, or a branched, saturated or a straight-chain or branched, unsaturated alkylene group of 2-10 carbon atoms, each of which can optionally be substituted by fluorine atoms, n is the number 1, 2 or 3, E is —C≡C— or —CR$_6$=CR$_7$— wherein R$_6$ and R$_7$ differ from each other and one is hydrogen and the other alkyl of 1-5 carbon atoms, or one is hydrogen and the other is halogen, or E can also be —CH$_2$CH$_2$— when R$_1$ is R$_3$, R$_4$ is C$_1$-C$_{10}$-alkyl, C$_{3-10}$-cycloalkyl, optionally substituted C$_6$-C$_{10}$-aryl or a heterocyclic group, R$_5$ is a free or functionally modified hydroxy group and, when R$_2$ is hydrogen, the salts thereof with physiologically compatible bases.

The compounds of this invention have hypotensive and bronchodilatory effects. They are furthermore suited for vasodilation, inhibition of thrombocyte aggregation and of gastric acid secretion, as well as for cytoprotection of the stomach, heart, liver, pancreas, and kidneys.

DETAILED DISCUSSION OF THE INVENTION

The compounds of Formula I include (5E)- as well as (5Z)-isomers.

Suitable alkyl groups R$_2$ and R$_3$ include straight- or branched-chain alkyl groups of 1-10 carbon atoms, for example, methyl, ethyl, propyl, isopropyl, butyl, isobutyl, tert-butyl, pentyl, isopentyl, neopentyl, heptyl, hexyl, decyl, etc. The alkyl groups R$_2$ and R$_3$ can optionally be mono- to polysubstituted (e.g., 2-4 substituents) by halogen atoms, hydroxy groups, C$_1$-C$_4$-alkoxy groups, optionally substituted C$_6$-C$_{10}$-aryl groups, di-C$_1$-C$_4$-alkylamines and tri-C$_1$-C$_4$-alkylammonium. Mono-substituted alkyl groups are preferred. Examples of suitable substituents include fluorine, chlorine or bromine atoms, phenyl, dimethylamino, diethylamino, methoxy, ethoxy. Suitable substituents on the aryl substituents are those described below for R$_1$ aryl groups, per se. Preferred alkyl groups R$_2$ and R$_3$ include those of 1-4 carbon atoms, e.g., methyl, ethyl, propyl, isobutyl, butyl, etc., dimethylaminopropyl also being preferred.

Suitable aryl groups R$_2$ and R$_3$ and in the aralkyl group R$_3$ include substituted as well as unsubstituted aryl groups, for example, phenyl, 1-naphthyl or 2-naphthyl, optionally substituted by 1-3 halogen atoms, a phenyl group, 1-3 alkyl groups of 1-4 carbon atoms each, or a chloromethyl, fluoromethyl, trifluoromethyl, carboxy, hydroxy or alkoxy group of 1-4 carbon atoms. Substituents in the 3- and 4-positions on the phenyl ring are preferred, for example, by fluorine, chlorine, alkoxy or trifluoromethyl or in the 4-position by hydroxy. The alkyl portion of the aralkyl group R$_3$ is as described for the other unsubstituted alkyl groups above.

The cycloalkyl groups R$_2$ and R$_3$ can contain 3-10, preferably 5 or 6 carbon atoms in the ring. The rings can be substituted by alkyl groups of 1-4 carbon atoms. Examples include cyclopentyl, cyclohexyl, methylcyclohexyl and adamantyl.

Suitable heterocyclic groups R$_2$ and R$_3$ include 5- and 6-membered heterocycles, preferably aromatic, containing at least one hetero atom, preferably nitrogen, oxygen or sulfur, the remaining being C-atoms. Examples include 2-furyl, 3-furyl, 2-thienyl, 3-thienyl, 2-pyridyl, 3-pyridyl, 4-pyridyl, etc.

The aryl residue in the

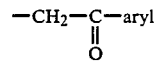

group of R$_2$ can be phenyl, or α- or β-naphthyl each of which can be substituted by 1-3 phenyl groups (each of which, in turn, can optionally be substituted by 1-3 halogen atoms, such as F, Cl or Br), or by 1-3 C$_1$-C$_4$-alkoxy groups or 1-3 halogen atoms (F, Cl, Br). Single substitutions by phenyl, C$_1$-C$_2$-alkoxy, chlorine or bromine are preferred.

The hydroxy groups R$_5$ and those in W can be functionally modified, for example by etherification or esterification wherein the free or modified hydroxy groups in W can be in the α- or β-position; free hydroxy groups are preferred. Suitable ether and acyl residues are those known to persons skilled in the art. Readily cleavable ether residues are preferred, e.g., the tetrahydropyranyl, tetrahydrofuranyl, α-tribenzylsilyl, etc., residues. Suitable acyl residues include those derived from hydrocarbon carboxylic or sulfonic acids, e.g., wherein the acyl moiety attached to the carbonyl group thereof is a group, for example, acetyl, propionyl, butyryl, benzoyl, etc.

The hydrocarbon aliphatic group R$_4$ can be straight-chained or branched, saturated or unsaturated, e.g., alkyl or alkenyl, preferably saturated, each of 1-10, especially 1-7 (2-7) carbon atoms which can optionally be substituted by aryl, which latter can be substituted, if desired, all as described for R$_1$ above. Examples include methyl, ethyl, propyl, butyl, isobutyl, tert-butyl, pentyl, hexyl, heptyl, octyl, butenyl, isobutenyl, propenyl, pentenyl, hexenyl, benzyl, p-chlorobenzyl, etc.

The cycloalkyl group R$_4$ can contain in the ring 3-10, preferably 3-6 carbon atoms. The rings can be substituted by alkyl groups of 1-4 carbon atoms. Examples include cyclopropyl, cyclobutyl, cyclopentyl, cyclohexyl, methylcyclohexyl and adamanyyl.

Substituted and unsubstituted aryl groups R$_4$ include, for example: phenyl, 1-naphthyl and 2-naphthyl, each of which can be substituted by 1-3 halogen atoms, a phenyl group, 1-3 alkyl groups of 1-4 carbon atoms each, a chloromethyl, fluoromethyl, trifluoromethyl, carboxy, C$_1$-C$_4$-alkoxy or hydroxy group. The substitution on the phenyl ring is in the 3- and 4-positions, preferably, for example, by fluorine, chlorine, C$_1$-C$_4$-alkoxy, or trifluoromethyl, or in the 4-position by hydroxy.

Suitable heterocyclic groups R$_4$ include 5- and 6-membered heterocycles, preferably aromatic, containing at least one hetero atom, preferably nitrogen, oxygen or sulfur, the remainder being C-atoms. Examples include 2-furyl, 2-thienyl, 2-pyridyl, 3-pyridyl, 4-pyridyl, 3-furyl, 3-thienyl, etc.

Suitable as the alkylene group D are straight-chain or branched-chain, saturated and unsaturated alkylene or alkenylene residues, preferably saturated ones of 1-10, especially 1-5 carbon atoms, all of which can optionally be substituted by fluorine atoms. Examples include: methylene, fluoromethylene, ethylene, 1,2-propylene, ethylethylene, trimethylene, tetramethylene, pentamethylene, 1-methyltetramethylene, 1-methyltrimethylene, etc.

The alkyl groups R$_6$ and R$_7$ represent straight-chained or branched, saturated alkyl groups of 1-4 carbon atoms as disclosed above for R$_2$ and R$_4$. R$_6$ and $R_7$ halogen atoms can be chlorine or bromine, preferably chlorine.

Suitable for salt formation with the free acids ($R_1$=H) are inorganic and organic bases as known to those skilled in the art for forming physiologically compatible salts. Examples include: alkali metal hydroxides, e.g., sodium and potassium hydroxide, alkaline earth metal hydroxides, e.g., calcium hydroxide, ammonia, amines, e.g., ethanolamine, diethanolamine, triethanolamine, N-methylglucamine, morpholine, tris(hydroxymethyl)methylamine, etc.

This invention furthermore relates to a process for preparing the compounds of Formula I which is characterized by reacting a compound of Formula II

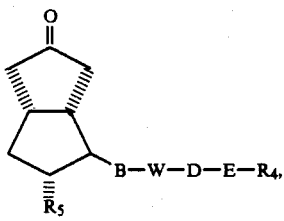

(II)

wherein $R_5$, W, D, E and $R_4$ have the above meanings and

B is a trans-double bond or a triple bond or a —CH=CBr-group, optionally after conventionally blocking any free hydroxy groups present, with a Wittig reagent of Formula III

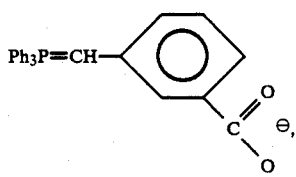

(III)

and optionally subsequently, in any desired sequence, separating isomers and/or liberating blocked hydroxy groups and/or esterifying or etherifying free hydroxy groups and/or saponifying an esterified carboxy group or converting a carboxy group with a physiologically compatible base into a salt, or reducing an esterified carboxy group, after blockage of free hydroxy groups, to the aldehyde by etherification with diisobutyl aluminum hydride, reacting with an organometallic compound, and thereafter oxidizing to the ketone.

The compounds of general Formula II can be reacted with the Wittig reagent of Formula III, which latter is produced from the corresponding phosphonium salt with methanesulfinylmethyl sodium or methanesulfinyl potassium or potassium tert-butylate in dimethyl sulfoxide or dimethyl sulfoxide - tetrahydrofuran mixtures, at temperatures of 0° C. to 100° C., preferably 20°-60° C., in an aproptic solvent or solvent mixture, preferably dimethyl sulfoxide, dimethylformamide or tetrahydrofuran. The separation of the thus-obtained Z- and E-configured olefins (5,6-position) takes place as usual, for example, by column or layer chromatography. During the precedingly described Wittig olefin-forming reaction, if B represents a CH=CBr-group, formation of the 13,14-acetylene bond occurs at the same time, with hydrogen bromide being split off.

Saponification of the prostaglandin esters is performed according to methods known to those skilled in the art, such as, for example, with alkaline catalysts.

Introduction of the group —$OR_2$ for $R_1$ wherein $R_2$ is an alkyl group of 1-10 carbon atoms takes place according to methods known to persons skilled in the art. The carboxy compounds ($R_2$=H) are reacted, for example, with diazo hydrocarbons in a manner known, per se. Esterification with diazo hydrocarbons takes place, for example, by mixing a solution of the diazo hydrocarbon in an inert solvent, preferably in diethyl ether, with the carboxy compound in the same or in another inert solvent, e.g., methylene chloride. After the reaction is finished within 1-30 minutes, the solvent is removed and the ester purified in the usual way. Dizoalkanes are either known or can be produced by conventional methods [Org. Reactions 8: 389-394 (1954)].

Introduction of the group —$OR_2$ for $R_1$ wherein $R_2$ is a substituted or unsubstituted aryl group also takes place according to methods known to those skilled in the art. The carboxy compounds can be reacted, for example, with the corresponding aryl hydroxy compounds with dicyclohexylcarbodiimide in the presence of a suitable base, e.g., pyridine or triethylamine, in an inert solvent. Suitable solvents include methylene chloride, ethylene chloride, chloroform, ethyl acetate, tetrahydrofuran, preferably chloroform. The reaction is performed at temperatures of −30° C. to +50° C., preferably about +10° C.

The compounds having $R_2$=heterocyclic or cycloalkyl are prepared analogously.

Introduction of the group $R_3$ for $R_1$ is effected according to methods known to persons skilled in the art. For example, the carboxylic acid esters are reduced to the aldehyde with diisobutyl aluminum hydride at low temperatures, preferably about −70° C., in inert solvent, such as, for example, toluene or tetrahydrofuran. The reaction of the aldehyde with an organolithium or organomagnesium compound to prepare the $R_3$ containing compound, can take place in an inert solvent or solvent mixture, e.g., diethyl ether, tetrahydrofuran, dioxane, toluene, preferably tetrahydrofuran or diethyl ether. The reaction is conducted at temperatures of −100° C. to 60° C., preferably at −70° C. to 30° C.

The organometallic compounds required for this reaction are prepared, for example, by reacting the corresponding halogen compound with an alkali or alkaline earth metal (magnesium) according to known processes.

The prostaglandin derivatives of general Formula I wherein $R_2$ is a hydrogen atom can be converted into salts with suitable amounts of the corresponding inorganic bases under neutralization conditions. For example, when dissolving the corresponding PG acids in water containing the stoichiometric quantity of the base, the solid inorganic salt is obtained after evaporation of the water or after addition of a water-miscible solvent, for example, alcohol or acetone.

The amine salts are produced as usual. For this purpose, the PG acid is dissolved, for example, in a suitable solvent, such as ethanol, acetone, diethyl ether or benzene, and at least the stoichiometric amount of the amine is added to this solution. During this process, the salt is usually obtained in the solid form, or is isolated as usual after evaporation of the solvent.

The functional modification of the free OH-groups takes place by means of methods known to those skilled in the art. For introducing the ether blocking groups, for example, the reaction is performed with dihydropyran in methylene chloride or chloroform with the use of an acidic condensation agent, e.g., p-toluenesulfonic acid. The dihydropyran is used in excess, preferably in four to ten times the amount required theoretically. The reaction is normally finished at 0° C. to 30° C. after 15-30 minutes.

The oxidation of the 1-hydroxy group can be effected according to the methods known to persons skilled in the art. Examples of suitable oxidizing agents are: pyridinium dichromate (Tetrahedron Letters 1979: 399), Jones reagent (J. Chem. Soc. 1953: 2555) or platinum/oxygen (Adv. in Carbohydrate Chem. 17: 169 [1962]) or Collins oxidation. Oxidation with pyridinium chromate is conducted at temperatures of 0° C. to 100° C., preferably 20°-40° C., in a solvent inert with respect to the oxidizing agent, for example, dimethylformamide. Oxidation with Jones reagent takes place at temperatures of −40° C. to +40° C., preferably 0°-30° C., in acetone as the solvent. Oxidation with platinum/oxygen is performed at temperatures of 0° C. to 60° C., preferably 20°-40° C., in a solvent inert with respect to the oxidizing agent, such as, for example, ethyl acetate.

Introduction of the acyl blocking groups is effected by reacting a compound of general Formula I conventionally with a carboxylic acid derivative, e.g., an acid chloride, acid anhydride, etc.

The liberation of a functionally modified OH-group to obtain the compounds of general Formula I takes place according to known methods. For example, ether blocking groups are split off in an aqueous solution of an organic acid, e.g., acetic acid, propionic acid, and others, or in an aqueous solution of an inorganic acid, e.g., hydrochloric acid. To improve solubility, a water-miscible, inert organic solvent is suitably added. Organic solvents that can be utilized are, for example, alcohols, such as methanol and ethanol, and ethers, such as dimethoxyethane, dioxane and tetrahydrofuran. Tetrahydrofuran is employed with preference. The splitting-off step is preferably conducted at temperatures of between 20° C. and 80° C.

The silyl ether blocking groups are split off, for example, with tetrabutylammonium fluoride. Examples of suitable solvents are tetrahydrofuran, diethyl ether, dioxane, methylene chloride, etc. The splitting-off step is preferably performed at temperatures of between 0° C. and 80° C.

The acyl groups are saponified, for example, with alkali or alkaline earth carbonates or hydroxides in an alcohol or in the aqueous solution of an alcohol. Suitable alcohols are aliphatic alcohols, such as, for example, methanol, ethanol, butanol, etc., preferably methanol. Suitable alkali carbonates and hydroxides are potassium and sodium salts, but the potassium salts are preferred. Examples of suitable alkaline earth carbonates and hydroxides are calcium carbonate, calcium hydroxide and barium carbonate. The reaction takes place at −10° C. to 70° C., preferably at 25° C.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparative methods, all starting materials are known or readily preparable from known starting materials. Of course, the compounds of this invention can also be used to prepare one another using the reactions discussed above and other conventional methods.

The compounds of Formula II serving as the starting material can be prepared conventionally according to the processes described in DOS's Nos. 2,845,770; 3,048,906; 3,121,155; 3,204,443; 3,209,702; 3,225,288; 3,226,550; 3,237,200; 3,206,123; and 3,306,125, or are already known.

The 1-carboxy or other $COOR_2$ compounds of this invention show hypotensive and bronchodilatory effects. They are furthermore suitable for inhibiting thrombocyte aggregation. The 1-keto (1-$COR_3$) compounds of this invention show a selective cytoprotective activity directed to the stomach, intestine, heart, to the liver, kidneys, and to the pancreas.

Consequently, the novel carbacyclin derivatives of Formula I constitute valuable pharmaceuticals. Moreover, they exhibit, as compared with corresponding prostaglandins, with a similar spectrum of activity, a higher specificity and, above all, a substantially prolonged duration of efficacy. As compared with $PGI_2$, they are distinguished by higher stability. The high tissue specificity of the novel prostaglandins is demonstrated in a study on smooth-muscle organs, such as, for example, on the guinea pig ileum or on the isolated rabbit trachea where a substantially lower stimulation can be observed than in the administration of natural prostaglandins of the E-, A- or F-type.

The novel carbacyclin analogs possess the properties typical for prostacyclins, such as, for example, lowering of peripheral arterial and coronary vascular resistance, inhibition of thrombocyte aggregation and dissolution of platelet thrombi, myocardial cytoprotection and thus lowering of systemic blood presure without simultaneously lower stroke volume and coronary blood flow; treatment for stroke, prophylaxis, and therapy of coronary heart disease, coronary thrombosis, cardiac infarction, peripheral arterial diseases, arteriosclerosis and thrombosis, prophylaxis and therapy of ischemic attacks of the CNS system, therapy for shock, inhibition of bronchoconstriction, inhibition of gastric acid secretion, cytoprotection for gastric and intestinal mucosa, cytoprotection in the liver, kidney, and in the pancreas; anti-allergic properties, lowering of pulmonary vascular resistance and pulmonary blood pressure, promotion of kidney blood flow, utilization in place of heparin or as adjuvant in dialysis of hemofiltration, preservation of blood plasma stores, especially blood platelet stores, inhibition of labor, treatment of gestational toxicosis, enhancement of cerebral blood flow, etc. Besides, the novel carbacyclin derivatives exhibit antiproliferative and antidiarrheogenic properties.

The carbacyclins of this invention can also be utilized in combination, for example, with β-blockers, diuretics, phosphodiesterase inhibitors, calcium antagonists, nonsteroidal anti-inflammatory agents, leukotriene synthesis inhibitors, leukotriene antagonists, thromboxane synthesis inhibitors or thromboxane antagonists.

The dosage of the compounds is 1–1,500 μg/kg/day when administered, e.g., to human patients for all uses, analogously to the known agent Iloprost. The unit dosage for the pharmaceutically acceptable carrier is 0.01–100 mg.

With intravenous injection administered to non-anesthetized, hypertonic rats in doses of 5, 20 and 100 μg/kg body weight, the compounds of this invention exhibit a stronger hypotensive effect and a longer lasting activity than $PGE_2$ and $PGA_2$ without triggering diarrhea, as does $PGE_2$, or cardiac arrhythmias, as does $PGA_2$.

Upon intravenous injection administered to anesthetized rabbits, the compounds of this invention show, as compared with $PGE_2$ and $PGA_2$, a stronger and considerably longer lasting lowering of blood pressure without affecting other smooth-muscle organs or organ functions.

Sterile, injectable, aqueous or oily solutions can be utilized for parenteral administration. Suitable for oral administration are, for example, tablets, dragees or capsules.

The invention accordingly also concerns medicinal agents based on the compounds of general Formula I and conventional auxiliary agents and excipients, including cyclodextrin clathrates. The active agents of this invention can serve, in conjunction with the auxiliary agents known and customary in galenic pharmacy, for example, for the preparation of hypotensors, thrombocyte aggregation inhibitors or cytoprotective agents.

The pharmacologically active compounds of this invention can be processed in accordance with conventional methods of galenic pharmacy to produce medicinal agents for administration to patients, e.g., mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Suitable dosages for a given host can be determined using conventional considerations, e.g., by customary comparison of the differential activities of the subject compound and of a known agent, e.g., by means of an appropriate, conventional pharmacological protocol. The novel carbacyclin analogs from clathrates with cyclodextrines.

The novel prostaglandin analogs of this invention are substantially more selective with regard to potency, as compared with known PG analogs, in causing prostaglandin-like biological responses, and have a substantially longer duration of biological activity. Accordingly, each of these novel prostaglandin analogs is surprisingly and unexpectedly more useful than one of the corresponding conventional prostaglandins for at least one of the pharmacological purposes indicated above because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(5E)-(16RS)-16-Methyl-18,18,19,19-tetradehydro-2,3,4-trinor-1,5-inter-m-phenylene-6a-carbaprostaglandin $I_2$ At 5° C., 4.48 g of potassium tert-butylate is added within 45 minutes to a solution of 10 g of triphenyl-3-carboxybenzylphosphonium bromide in 24 ml of dimethyl sulfoxide and 14 ml of tetrahydrofuran; the mixture is stirred for 45 minutes at 5° C. To the red ylene solution is added a solution of 1.8 g of (1R,5S,6R,7R)-7-(tetrahydropyran-2-yloxy)-6-[(E)-(3S,4RS)-4-methyl-3-(tetrahydropyran-b 2-yloxy)oct-1-en-6-ynyl]bicyclo[3.3.0]octan-3-one in 16 ml of tetrahydrofuran, and the mixture is stirred for 18 hours at 35° C. The reaction mixture is poured on ice water, acidified with citric acid to pH 5 and extracted with methylene chloride. The organic phase is shaken with brine, dried over magnesium sulfate and evaporated under vacuum. The residue is purified by repeated chromatography on silica gel. With hexane/ethyl acetate (6+4), the products are first 390 mg of the Z-configured olefin, 0.9 g of unseparated 5E/Z mixture, as well as, being the more polar component, 370 mg of (5E)-(16RS)-16-methyl-18,18,19,19-tetradehydro-2,3,4-trinor-1,5-inter-m-phenylene-6a-carbaprostaglandin $I_2$ 11,15-bis(tetrahydropyranyl ether) as a colorless oil.

IR ($CHCl_3$): 3605, 3400 (broad), 2950, 2868, 1695 (broad), 1600, 1573, 1380, 974 $cm^{-1}$.

To split off the blocking groups, 370 mg of the above-obtained product is stirred with 40 ml of a mixture of acetic acid/water/tetrahydrofuran (65/35/10) for 20 hours at 25° C. Then the mixture is evaporated under vacuum while adding toluene, and the residue is chromatographed on silica gel. With methylene chloride/isopropanol (9+1), 205 mg of the title compound is obtained as a colorless oil.

IR: 3605, 3400 (broad), 2960, 2920, 1695 (broad), 1600, 1582, 970 cm$^{-1}$.

EXAMPLE 2

(5Z)-(16RS)-16-Methyl-18,18,19,19-tetradehydro-2,3,4-trinor-1,5-inter-m-phenylene-6a-carbaprostaglandin I$_2$ 390 mg of the (5Z)-configured olefin obtained after separation by chromatography in Example 1 is agitated for 18 hours at 25° C. with 40 ml of a mixture of acetic acid/water/tetrahydrofuran (65/35/10), evaporated under vacuum while adding toluene, and the residue chromatographed on silica gel. With methylene chloride/isopropanol (9+1), 220 mg of the title compound is obtained as an oil.

IR: 3605, 3400 (broad), 2960, 2920, 1730, 1695, 1600, 1581, 970 cm$^{-1}$.

EXAMPLE 3

(5E)-(16RS)-16,20-Dimethyl-18,18,19,19-tetradehydro-2,3,4-trinor-1,5-inter-m-phenylene-6a-carbaprostaglandin I$_2$ Analogously to Example 1, 1.6 g of (1R, 5S, 6R, 7R)-7-(tetrahydropyran-2-yloxy)-6-[(E)-(3S,4RS)-4-methyl-3-(tetrahydropyran-2-yloxy)non-1-en-6-ynyl]-bicyclo[3.3.0]octan-3-one yields 420 mg of (5E)-(16RS)-16,16-dimethyl-18,18,19,19-tetradehydro-2,3,4-trinor-1,5-inter-m-phenylene-6a-carbaprostaglandin I$_2$ 11,15-bis(tetrahydropyranyl ether) as a colorless oil.

IR: 3600, 3410 (broad), 2950, 2869, 1696 (broad), 1600, 1573, 975 cm$^{-1}$.

After splitting off the blocking groups according to Example 1, 280 mg of the title compound is obtained as a colorless oil.

IR: 3600, 3380 (broad), 2962, 2922, 1696 (broad), 1600 1573, 971 cm$^{-1}$.

EXAMPLE 4

(5E)-18,18,19,19-Tetradehydro-16,16,20-trimethyl-2,3,4-trinor-1,5-inter-m-phenylene-6a-carbaprostaglandin I$_2$ In analogy to Example 1, 1.4 g of (1R,5S,6R,7R)-7(tetrahydropyran-2-yloxy)-6-[(E)-(3R)-4,4-dimethyl-3-(tetrahydropyran-2-yloxy)non-1-en-6-ynyl]bicyclo[3.3.0]octan-3one yields as the product 390 mg of (5E)-18,18,19,19-tetradehydro-16,16,20-trimethyl-2,3,4-trinor-1,5-inter-m-phenylene-6a-carbaprostaglandin I$_2$ 11,15-bis(tetrahydropyranyl ether) as a colorless oil.

IR: 3600, 3400 (broad), 2960, 2925, 1697 (broad), 1600, 1574, 972 cm$^{-1}$.

EXAMPLE 5

(5E)-20-Methyl-18,18,19,19-tetradehydro-16,16-trimethylene-2,3,4-trinor-1,5-inter-m-phenylene-6a-carbaprostaglandin I$_2$ Analogously to Example 1, 2 g of (1R,5S,6R,7R)-7-(tetrahydropyran-2-yloxy)-6-[(E)-(3R)-4,4-trimethylene-3-(tetrahydropyran-2-yloxy)non-1-en-6-ynyl]bicyclo[3.3.0]octan-3-one yields 595 mg of (5E)-20-methyl-18,18,19,19-tetradehydro-16,16-trimethylene-2,3,4-trinor-1,5-inter-m-phenylene-6a-carbaprostaglandin I$_2$11,15-bis(tetrahydropyranyl ether) as a colorless oil.

IR: 3600, 3400 (broad), 2950, 2885, 1698 (broad), 1600, 1580, 976 cm$^{-1}$.

After the blocking groups have been split off according to Example 1, 275 mg of the title compound is obtained as a colorless oil.

IR: 3600, 3400 (broad), 2955, 2895, 1695 (broad), 1600, 1580, 976 cm$^{-1}$.

EXAMPLE 6

(5E)-(16RS)-13,14-Didehydro-16-methyl-18,18,19,19-tetradehydro-2,3,4-trinor-1,5-inter-m-phenylene-6a-carbaprostaglandin I$_2$ In analogy to Example 1, 1.50 g of (1R,5S,6R,7R)-7(tetrahydropyran-2-yloxy)-6-[(3S,4RS)-4-methyl-3-(tetrahydropyran-2-yloxy)octa-1,6-diynyl]bicyclo[3.3.0]octan-3-one produces 460 mg of (5E)-(16RS)-13,14-didehydro-16-methyl-18,18,19,19-tetradehydro-2,3,4-trinor-1,5-inter-m-phenylene-6a-carbaprostaglandin I$_2$ 11,15-bis(tetrahydropyranyl ether) as a colorless oil.

IR: 3600, 3405 (broad), 2955, 2877, 2215, 1698 (broad), 1600, 1581 cm$^{-1}$.

After the blocking groups have been split off as described in Example 1, 251 mg of the title compound is obtained as a colorless oil.

IR: 3600, 3400 (broad), 2961, 2928, 2212, 1698 (broad), 1601, 1579 cm$^{-1}$.

EXAMPLE 7

(5E)-(16S)-13,14-Didehydro-16,20-dimethyl-18,18,19,19-tetradehydro-2,3,4-trinor-1,5-inter-m-phenylene-6a-carbaprostaglandin I$_2$ In analogy to Example 1, 2.0 g of (1R,5S,6R,7R)-7-(tetrahydropyran-2-yloxy)-6-[(3S,4S)-4-methyl-3-(tetrahydropyran-2-yloxy)nona-1,6-diynyl]-bicyclo[3.3.0]octan-3-one yields 590 mg of (5E)-(16S)-13,14-didehydro-16,20-dimethyl- 18,18,19,19-tetradehydro-2,3,4-trinor-1,5-inter-m-phenylene-6a-carbaprostaglandin I$_2$ 11,15-bis(tetrahydropyranyl ether) as a colorless oil.

IR: 3600, 3400 (broad), 2958, 2875, 2230, 1695 (broad), 1600, 1582 cm$^{-1}$.

After splitting off the blocking groups according to Example 1, 280 mg of the title compound is obtained as a colorless oil.

IR: 3600, 3400 (broad), 2960, 2924, 2230, 1696 (broad), 1600, 1579 cm$^{-1}$.

EXAMPLE 8

(5E)-13,14-Didehydro-20-methyl-18,18,19,19-tetradehydro-16,16-trimethylene-2,3,4-trinor-1,5-inter-m-phenylene-6a-carbaprostaglandin I$_2$ In analogy to Example 1, 1.05 g of (1R,5S,6R,7R)-7-(tetrahydropyran-2-yloxy)-6-[(3S)-4,4-trimethylene-3-(tetrahydropyran-2-yloxy)nona-1,6-diynyl]bicyclo[3.3.0]octan-3-one produces 310 mg of (5E)-13,14-didehydro-20-methyl-18,18,19,19-tetradehydro-16,16-trimethylene-2,3,4-trinor-1,5-inter-m-phenylene-6a-carbaprostaglandin I$_2$ 11,15-bis(tetrahydropyranyl ether) as a colorless oil.

IR: 3600, 3405 (broad), 2962, 2881, 2225, 1696 (broad), 1600, 1582 cm$^{-1}$.

After the blocking groups have been split off as in Example 1, 140 mg of the title compound is obtained as a colorless oil.

IR: 3600, 3410 (broad), 2960, 2931, 2225, 1698 (broad), 1578 cm$^{-1}$.

EXAMPLE 9

(3E)-(1S,5S,6S,7R)-3-(m-Acetylbenzylidene)-7-hydroxy-6-[(E)-(3S,4RS)3-hydroxy-4-methyloct-1-en-6-ynyl]-bicyclo[3.3.0]octane At 0° C., a solution of 2.0 g of (5E)-(16RS)-16-methyl-18,18,19,19-tetradehydro-2,3,4-trinor-1,5-inter-m-phenylene-6a-carbaprostaglandin I$_2$ 11,15-bis(tetrahydropyranyl ether) (see Example 1) in 100 ml of dichloromethane is combined dropwise with such a quantity of ethereal diazomethane solution that a weak yellow coloring of the reaction solution persists. Subsequently the residue is evaporated under vacuum and dissolved in 130 ml of toluene. At −70° C., 6.2 ml of a 1.2-molar solution of diisobutyl aluminum hydride in toluene is added dropwise and the mixture is stirred for 30 minutes at −70° C. Then, in succession, 2.5 ml of isopropanol and 2.5 ml of water are dropped into the mixture and the latter is agitated for 2 hours at 20° C., filtered, and evaporated under vacuum. The residue is chromatographed on silica gel with hexane/ether (1:1), thus obtaining 1.51 g of (3E)-(1S,5S,6S,7R)-3-(m-formylbenzylidene)-6-[(E)-(3S,4RS)-4-methyl-3-(tetrahydropyran-2-yloxy)oct-1-en-6-ynyl]-7-(tetrahydropyran-2-yloxy)bicyclo[3.3.0]octane.

1.40 g of the aldehyde, produced as above, is dissolved in 40 ml of diethyl ether and 40 ml of tetrahydrofuran and, at −70° C., 5 ml of a 1.6-molar ethereal methyl lithium solution is added dropwise thereto. The mixture is allowed to warm up to 0° C. within one hour and diluted with saturated ammonium chloride solution, extracted with ether, washed with brine, and dried over magnesium sulfate whereafter the product is evaporated under vacuum, thus obtaining an oily crude product.

In order to convert the thus-obtained carbinol into the methyl ketone, the residue is dissolved in 50 ml of dichloromethane and this solution is added to 6 g of Collins reagent in 80 ml of dichloromethane. After 15 minutes, the mixture is combined with 300 ml of ether, filtered, and the filtrate washed in succession with water, 5% sodium bicarbonate solution, 10% strength sulfuric acid, and water, dried over magnesium sulfate, and evaporated under vacuum.

In order to split off the blocking groups, the evaporation residue is stirred for 16 hours at 20° C. with 100 ml of acetic acid/water/tetrahydrofuran (65/35/10), evaporated under vacuum, and the residue chromatographed on silica gel with ethyl acetate/hexane (7+3), thus obtaining 510 mg of the title compound as a colorless oil.

IR: 3600, 3405 (broad), 2938, 1692, 1601, 976 cm$^{-1}$.

EXAMPLE 10

(3E)-(1S,5S,6S,7R)-3-(m-Acetylbenzylidene)-6-[(E)-(3S)-3-cyclohexyl-3-hydroxyl-1-propenyl]-7-hydroxybicyclo[3.3.0]octane In analogy to Example 9, 1 g of (5E)-15-cyclohexyl-16,17,18,19,20-pentanor-2,3,4-trinor-1,5-inter-m-phenylene-6a-carbaprostaglandin I$_2$ 11,15-bis(tetrahydropyranyl ether) yields 220 mg of the title compound as a colorless oil.

IR: 3600, 3425 (broad), 2980, 2935, 1688, 1600, 1581, 975 cm$^{-1}$.

EXAMPLE 11

(5E)-(16RS)-16-Methyl-18,18,19,19-tetradehydro-2,3,4-trinor-1,5-inter-m-phenylene-6a-carbaprostaglandin I$_2$ Methyl Ester At 0° C., an ethereal solution of diazomethane is added dropwise to a solution of 150 mg of (5E)-(16RS)-16-methyl-18,18,19,19-tetradehydro-2,3,4-trinor-15-m-inter-phenylene-6a-carbaprostaglandin I$_2$ in 10 ml of dichloromethane until the mixture assumes a permanent yellow color. Then the mixture is evaporated under vacuum and the residue chromatographed on silica gel with ethyl acetate/hexane (8+2), yielding 115 mg of the title compound as a colorless oil.

IR: 3600, 2955, 2864, 1710, 1601, 1578, 975 cm$^{-1}$.

EXAMPLE 12

(5E)-(16RS)-16-Methyl-18,18,19,19-tetradehydro-2,3,4-trinor-1,5-inter-m-phenylene-6a-carbaprostaglandin I$_2$ Phenacyl Ester 220 mg of (5E)-(16RS)-16-methyl-18,18,19,19-tetradehydro-2,3,4-trinor-1,5-m-inter-phenylene-6a-carbaprostaglandin I$_2$ is dissolved in 10 ml of acetone, combined with 135 mg of ω-bromoacetophenone and 1.5 ml of triethylamine and agitated overnight at room temperature. The mixture is diluted with ether, shaken in succession with water and brine, dried over magnesium sulfate, and evaporated under vacuum. The residue is purified by chromatography on silica gel with dichloromethane/10% acetone, thus obtaining 209 mg of the title compound.

IR: 3600, 2965, 2862, 1705 (broad), 1600, 1581, 974 cm$^{-1}$.

EXAMPLE 13

(5E)-(16RS)-16-Methyl-18,18,19,19-tetradehydro-2,3,4-trinor-1,5-inter-m-phenylene-6a-carbaprostaglandin I$_2$ Tris(hydroxymethyl)aminomethane Salt At 70° C., a solution of 60 mg of tris(hydroxymethyl)aminomethane in 0.2 ml of water is added to a solution of 185 mg of (5E)-(16RS)-16-methyl-18,18,19,19-tetradehydro-2,3,4-trinor-1,5-m-inter-phenylene-6a-carbaprostaglandin I$_2$ in 40 ml of acetonitrile. The mixture is allowed to cool under agitation, decanted from the solvent after 16 hours, and the residue dried under vacuum, yielding 159 mg of the title compound as a waxy mass.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A carbacyclin derivative of the formula

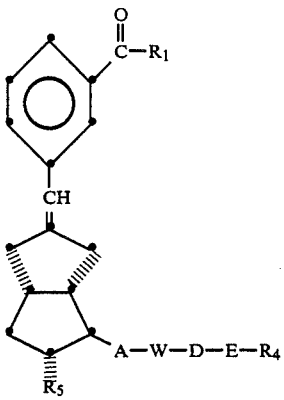

wherein

R₁ is OR₂ wherein R₂ is (a) hydrogen, or (b) a C₁₋₄-alkyl group,

A is trans —CH=CH— or —C≡C—,

W is an α- or β-hydroxymethylene group,

D is a straight or branched ethylene group of up to 5 carbon atoms

E is —C≡C—,

R₄ is a C₁₋₇ alkyl radical,

R₅ is OH, or for said compounds wherein R₂ is H, a physiologically compatible salt thereof with a base.

2. A compound of claim 1, wehrein R₁ is OH.

3. A compound of claim 1, wherein A-W-D-E-R₄ is

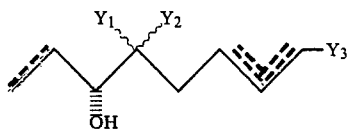

wherein Y₁/Y₂ represent H, CH₃ or CH₃, CH₃

represents is a double or triple bond; and Y₃ represents H or CH₃.

4. (5E)-(16RS)-16-Methyl-18,18,19,19-tetradehydro-2,3,4-trinor-1,5-inter-m-phenylene-6a-carbaprostaglandin I₂, a compound of claim 1.

5. (5Z)-(16RS)-16-Methyl-18,18,19,19-tetradehydro-2,3,4-trinor-1,5-inter-m-phenylene-6a-carbaprostaglandin I₂, a compound of claim 1.

6. (5E)-(16RS)-16-20-Dimethyl-18,18,19,19-tetradehydro-2,3,4-trinor-1,5-inter-m-phenylene-6a-carbaprostaglandin I₂, a compound of claim 1.

7. (5E)-18,18,19,19-Tetradehydro-16,16,20-trimethyl-2,3,4-trinor-1,5-inter-m-phenylene-6a-carbaprostaglandin I₂, a compound of claim 1.

8. (5E)-(16RS)-13,14-Didehydro-16-methyl-18,18,19,19-tetradehydro-2,3,4-trinor-1,5-inter-m-phenylene-6a-carbaprostaglandin I₂, a compound of claim 1.

9. (5E)-(16S)-13,14-Didehydro-16,20-dimethyl-18,18,19,19-tetradehydro-2,3,4-trinor-1,5-inter-m-phenylene-6a-carbaprostaglandin I₂, a compound of claim 1.

10. (5E)-(16RS)-16-Methyl-18,18,19,19-tetradehydro-2,3,4-trinor-1,5-inter-m-phenylene-6a-carbaprostaglandin I₂ Tris(hydroxymethyl)aminomethane Salt, a compound of claim 1.

11. A pharmaceutical composition comprising a finite amount of a compound of claim 1, and a pharmaceutically acceptable carrier.

12. A composition of claim 11, wherein said amount is 0.01 to 100 mg.

13. A method of lowering blood pressure in a patient comprising administering a compound of claim 1.

14. A method of achieving a bronchodilatory effect in a patient comprising administering a compound of claim 1.

* * * * *

UNITED STATES PATENT AND TRADEMARK OFFICE
CERTIFICATE OF CORRECTION

PATENT NO. : 4,827,017
DATED : May 2, 1989
INVENTOR(S) : Werner Skuballa et al

It is certified that error appears in the above-identified patent and that said Letters Patent is hereby corrected as shown below:

Column 16, first formula should read -- 

Column 16, line 12: reads "is a double or triple bond; and $Y_3$ represents H or $CH_3$."

should read -- ======== is a double or triple bond; and $Y_3$ represents H or $CH_3$ --

Signed and Sealed this

Fifteenth Day of August, 1989

Attest:

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,827,017
DATED : May 2, 1989
INVENTOR(S) : Skuballa et al It is certified that error appears in the above-identified patent and that said Letters Patent is hereby corrected as shown below:

Cover Page, Right Column, Third Formula:

Should Read:-- 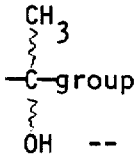 --

Column 1, First Formula:

Should Reads: "  "   Should Read: -- 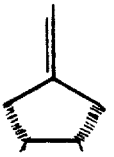 --

Signed and Sealed this

Fifth Day of June, 1990

*Attest:*

HARRY F. MANBECK, JR.

*Attesting Officer*   *Commissioner of Patents and Trademarks*